United States Patent [19]
Skotnicki et al.

[11] Patent Number: 5,391,730
[45] Date of Patent: Feb. 21, 1995

[54] PHOSPHORYLCARBAMATES OF RAPAMYCIN AND OXIME DERIVATIVES THEREOF

[75] Inventors: Jerauld S. Skotnicki, Allentown; Andri L. Smith, Princeton, both of N.J.

[73] Assignee: American Home Products Corporation, Madison, N.J.

[21] Appl. No.: 134,428

[22] Filed: Oct. 8, 1993

[51] Int. Cl.$^6$ .................. A61K 31/395; C07D 491/06
[52] U.S. Cl. ...................................... 540/456
[58] Field of Search .................... 540/456; 514/291

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 424/122 |
| 4,375,464 | 3/1993 | Sehgal et al. | 424/122 |
| 4,401,653 | 8/1983 | Eng | 424/114 |
| 4,650,803 | 3/1987 | Stella et al. | 514/291 |
| 4,885,171 | 12/1989 | Surendra et al. | 424/122 |
| 5,023,262 | 6/1991 | Caufield et al. | 514/291 |
| 5,023,263 | 6/1991 | Von Burg | 514/291 |
| 5,023,264 | 6/1991 | Caufield et al. | 514/291 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 514/183 |
| 5,100,899 | 3/1992 | Calne | 514/291 |
| 5,102,876 | 4/1992 | Caufield | 514/183 |
| 5,118,677 | 6/1992 | Caufield | 514/183 |
| 5,118,678 | 6/1992 | Kao et al. | 514/183 |
| 5,120,842 | 6/1992 | Failli et al. | 514/452 |
| 5,130,307 | 7/1992 | Failli et al. | 514/321 |
| 5,138,051 | 8/1992 | Hughes et al. | 540/456 |
| 5,151,413 | 9/1992 | Caufield et al. | 514/63 |
| 5,169,851 | 12/1992 | Hughes et al. | 514/291 |
| 5,177,203 | 1/1993 | Failli et al. | 540/456 |
| 5,194,447 | 3/1993 | Kao | 514/542 |
| 5,221,670 | 6/1993 | Caufield | 514/183 |
| 5,233,036 | 8/1993 | Hughes | 540/455 |

FOREIGN PATENT DOCUMENTS

507555A1 7/1992 European Pat. Off. ............ 514/291

OTHER PUBLICATIONS

Kao et al., Commonly owned U.S. patent application Ser. No. 08/054,655 filed: Apr. 23, 1993.
Venzina, C. J. Antibiot. 28:721 (1975).
Sehgal, S. N., J. Antibiot. 28:727 (1975).
Baker, H. J., Antibiot. 31:539 (1978).
Martel, R. R., Can. J. Phyisol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M. Transplantation Proc. 23:507 (1991).

*Primary Examiner*—Robert T. Bond
*Attorney, Agent, or Firm*—Arnold S. Milowsky

[57] ABSTRACT

A compound of the structure

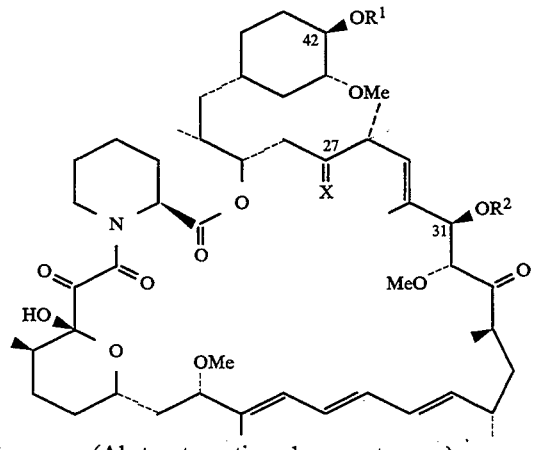

(Abstract continued on next page.)

wherein $R^1$ and $R^2$ are each, independently, hydrogen, or

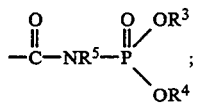

$R^3$ and $R^4$ are each, independently, hydrogen, Ar, or $-(CR^6R^7)_aY(CR^8R^9)_bZ$, or $R^3$ and $R^4$ may be taken together to form a 5-7 membered ring;

$R^5$ is hydrogen, alkyl, alkenyl, alkynyl, alkoxyalkyl, arylalkyl, cycloalkyl, or Ar;

$R^6$, $R^7$, $R^8$, and $R^9$, are each, independently, hydrogen, alkyl, alkenyl, alkynyl, hydroxyalkyl, alkoxyalkyl, alkylthioalkyl, alkylaminoalkyl, dialkylaminoalkyl, arylalkyl, cycloalkyl, $-OR^{10}$, $-SR^{10}$, halogen, $-CN$, $-NO_2$, $-CF_3$, $-COR^{10}$, $-CO_2R^{10}$, $-CONHR^{10}$, $-SO_2R^{10}$, $-SO_3R^{10}$, $-OSO_3R^{10}$, $-NR^{10}R^{11}$, $-NHCOR^{10}$, $-NHCO_2R^{10}$, $-NHSO_2R^{10}$, $-NHSO_3R^{10}$, or Ar;

X is O or $NOR^{12}$;

Y is $-O-$, $-CH_2-$, $-NR^{13}-$, $-S-$, $-S(O)-$, $-S(O)_2-$, or $-C(O)-$;

$R^{10}$, $R^{11}$, $R^{12}$, and $R^{13}$ are each, independently, hydrogen, alkyl, or arylalkyl;

Z is hydrogen, alkyl of 1-6 carbon atoms, or Ar;

Ar is aryl which may be optionally mono-, di-, or tri-substituted;

a = 1-6 and;

b = 0-6;

or a pharmaceutically acceptable salt thereof, with the proviso that $R^1$ and $R^2$ are not both hydrogen; and further provided that when a is greater than 1, each of the $(CR^6R^7)$ subunits may be the same or different and when b is greater than 1, each of the $(CR^8R^9)$ may be the same or different which is useful as an immunosuppressive, antiinflammatory, antifungal, antiproliferative, and antitumor agent.

9 Claims, No Drawings

PHOSPHORYLCARBAMATES OF RAPAMYCIN AND OXIME DERIVATIVES THEREOF

BACKGROUND OF THE INVENTION

This invention relates to phosphorylcarbamates of rapamycin and oxime derivatives thereof and a method for using them for inducing immunosuppression, and in the treatment of transplantation rejection, host vs. graft disease, autoimmune diseases, diseases of inflammation, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)]disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 21 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions. U.S. Pat. No. 5,118,678 discloses carbamates of rapamycin that are useful as immunosuppressive, antiinflammatory, antifungal, and antitumor agents. U.S. Pat. No. 5,194,447 discloses sulfonyl carbamates useful as immunosuppressive, anti-inflammatory, antifungal, and antitumor agents. U.S. Pat. No. 5,023,264 discloses oximes of rapamycin useful as immunosuppressive, anti-inflammatory, and antifungal agents.

DESCRIPTION OF THE INVENTION

This invention provides derivatives of rapamycin which are useful as immunosuppressive, antiinflammatory, antifungal, antiproliferative, and antitumor agents having the structure

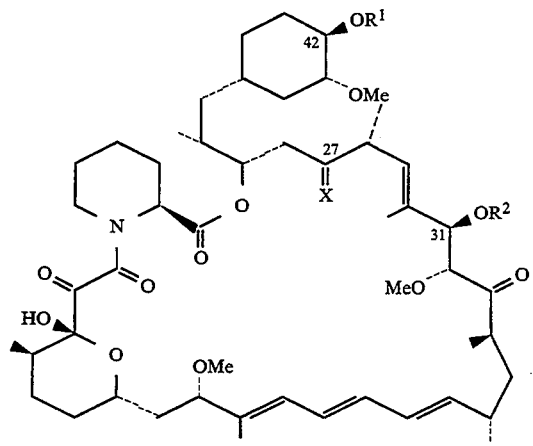

wherein $R^1$ and $R^2$ are each, independently, hydrogen, or

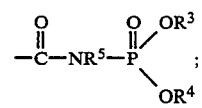

$R^3$ and $R^4$ are each, independently, hydrogen, Ar, or —$(CR^6R^7)_aY(CR^8R^9)_bZ$, or $R^3$ and $R^4$ may be taken together to form a 5–7 membered ring;

$R^5$ is hydrogen, alkyl of 1–6 carbon atoms, alkenyl of 2–7 carbon atoms, alkoxyalkyl of 2–7 carbon atoms, arylalkyl of 7–10 carbon atoms, cycloalkyl of 3–8 carbon atoms, or Ar;

$R^6$, $R^7$, $R^8$, and $R^9$, are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, —$OR^{10}$, —$SR^{10}$, halogen, —CN, —$NO_2$, —$CF_3$, —$COR^{10}$, —$CO_2R^{10}$, —$CONHR^{10}$, —$SO_2R^{10}$, —$SO_3R^{10}$, —$OSO_3R^{10}$, —$NR^{10}R^{11}$, —$NHCOR^{10}$, —$NHCO_2R^{10}$, —$NHSO_2R^{10}$, —$NHSO_3R^{10}$, or Ar;

X is O or $NOR^{12}$;

Y is —O—, —$CH_2$—, —$NR^{13}$—, —S—, —S(O)—, —$S(O)_2$—, or —C(O)—;

$R^{10}$, $R^{11}$, $R^{12}$, and $R^{13}$ are each, independently, hydrogen, alkyl of 1–6 carbon atoms, or arylalkyl of 7–10 carbon atoms;

Z is hydrogen, alkyl of 1–6 carbon atoms, or Ar;

Ar is aryl which may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, —$PO_3H$, and —$CO_2H$;

a=1–6 and;

b=0–6;

or a pharmaceutically acceptable salt thereof, with the proviso that $R^1$ and $R^2$ are not both hydrogen; and further provided that when a is greater than 1, each of the $(CR^6R^7)$ subunits may be the same or different and when b is greater than 1, each of the $(CR^8R^9)$ may be the same or different.

It is preferred that the aryl moiety of the Ar group or of the arylalkyl group is a phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, benzopyranyl, benz[b]thiophenolyl, benzimidazolyl, benzthiazolyl, benzodioxolyl, piperidyl, morpholinyl, piperazinyl, tetrahydrofuranyl, or pyrrolidinyl group which may be optionally mono-, di-, or tri-substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, $-SO_3H$, $-PO_3H$, and $-CO_2H$. It is more preferred that the aryl moiety is a phenyl group that may be optionally substituted as described above.

When $R^3$ and $R^4$ are defined as being taken together to form a 5-7 membered ring, it is preferred that $R^3R^4$ are $-(CH_2)_2-$, $-(CH_2)_3-$, or $-(CH_2)_4-$.

When X is $NOR^{13}$, the 27-oxime can exist in both the E and the Z forms; this disclosure covers both of these forms.

The pharmaceutically acceptable salts are those derived from such inorganic cations such as sodium, potassium, and the like; organic bases such as: mono-, di-, and trialkyl amines of 1-6 carbon atoms, per alkyl group and mono-, di-, and trihydroxyalkyl amines of 1-6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

Of these compounds, preferred members are those in which $R^3$ and $R^4$ are alkyl of 1-6 carbon atoms; those in which $R^5$ is hydrogen; those in which $R^2$ and $R^5$ are hydrogen; and those in which $R^2$ and $R^5$ are hydrogen and $R^3$ and $R^4$ are alkyl of 1-6 carbon atoms.

The compounds of this invention in which $R^5$ is hydrogen, that are carbamylated at the 42-position or at both the 31- and 42-positions can be prepared by reacting rapamycin with an isocyanate having the general structure

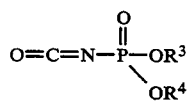

either in the presence of a base, such as pyridine, or in the absence of a base.

The 31-carbamylated compounds of this invention in which $R^5$ is hydrogen can be prepared by protecting the 42-alcohol of rapamycin with a protecting group, such as with a tert-butyl dimethylsilyl group, followed by carbamylation of the 31-position with an isocyanate with the general structure shown above. Removal of the protecting group provides the 31-carbamylated compounds. In the case of the tert-butyl dimethylsilyl protecting group, deprotection can be accomplished under mildly acidic conditions. The protection and deprotection of the 42-hydroxyl group of rapamycin was disclosed in U.S. Pat. No. 5,120,842, which is hereby incorporated by reference.

Having the 31-position carbamylated and the 42-position deprotected, the 42-position can be reacted with a different isocyanate than was reacted with the 31-alcohol, to give compounds having different carbamates at the 31- and 42-positions. Alternatively, the 42-carbamylated compounds, prepared as described above, can be reacted with a different isocyanate to provide compounds having different carbamates at the 31- and 42-positions.

For the compounds of this invention in which $R^5$ is hydrogen or is a substituent other than hydrogen, carbamates can be formed at the 42- and at the 31- and 42-positions by first convening rapamycin to a carbonate by reacting rapamycin with a suitable chloroformate, such as p-nitrophenyl chloroformate, followed by reaction of the carbonate with an appropriately substituted phosphoramidate anion, as shown in the scheme below.

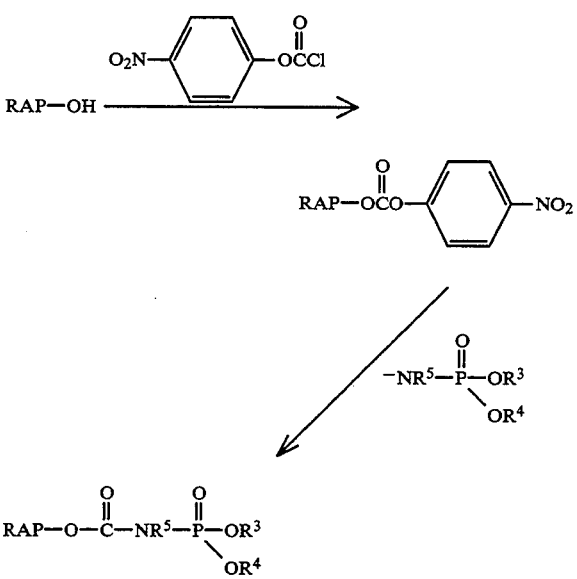

The phosphoramidate anion can be generated by treating the appropriate phosphoramidate with a strong base, such as sodium hydride or lithium diisopropylamide, at low temperatures, typically $-78°$ C. The 31-carbamylated compounds of this invention can be prepared using this route by first protecting the 42-position as described above, followed by conversion of the 31-hydroxyl group to a carbonate and subsequent treatment with a phosphoramidate anion.

For the compounds of this invention in which X is $NOR^{12}$, the oximation of the 27-ketone of rapamycin can be accomplished following the carbamylation by treatment of the rapamycin phosphonylcarbamate with an appropriately substituted hydroxylamine, as disclosed in U.S. Pat. No. 5,023,264, which is hereby incorporated by reference.

The isocyanates, phosphoramidates, and hydroxylamines used to prepare the compounds of the invention am commercially available or can be prepared by methods that are disclosed in the literature.

This invention also covers analogous carbamates of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1 -, 3 -, and/or 5-positions have been reduced [U.S. Pat. No. 5,023,262]; 42-oxorapamycin [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; and 15-hydroxy- and 15,27-bishydroxy-rapamycin [U.S. Pat. No. 5,102,876]. The disclosures in the above cited U.S. Patents are hereby incorporated by reference.

This invention additionally covers derivatives of rapamycin in which one of the 31 - or 42-hydroxyl groups has been converted to a phosphorylcarbamate, as described above, and the other of the 31 - or 42-hydroxyl groups has been esterified with a moiety that is not a phosphonylcarbamate. Such other esters include acyl derivatives of rapamycin as described in U.S. Pat. No. 4,316,885, which is hereby incorporated by reference; fluorinated esters of rapamycin as described in U.S. Pat. No. 5,100,883, which is hereby incorporated by reference; amide esters of rapamycin as described in U.S. Pat. No. 5,118,677, which is hereby incorporated by reference; carbamates of rapamycin as described in U.S. Pat. No. 5,118,678, which is hereby incorporated by reference; aminoesters of rapamycin as described in U.S. Pat. No. 5,130,337, which is hereby incorporated by reference; ethers and acetals of rapamycin as described in U.S. Pat. No. 5,151,413, which is hereby incorporated by reference; aminoacyl esters of rapamycin as described in U.S. Pat. No. 4,650,803, which is hereby incorporated by reference; sulfonates and sulfamates of rapamycin as described in U.S. Pat. No. 5,117,203; silyl ethers of rapamycin as described in U.S. Pat. No. 5,120,842, which is hereby incorporated by reference; and sulfonylcarbamates of rapamycin as described in U.S. Pat. No. 5,194,447, which is hereby incorporated by reference. Similarly, this invention covers compounds in which one hydroxyl of rapamycin has been converted to a phosphonyl carbamate and the other hydroxyl is an inorganic ester of the hydroxyl group. These esters include phosphate, nitrate, sulfinate, sulfonate esters, and the like, and organic esters of these inorganic acids.

Immunosuppressive activity for representative compounds of this invention was evaluated in an in vitro standard pharmacological test procedure to measure lymphocyte proliferation (LAF) and in an in vivo standard pharmacological test procedure which evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from nondrug treated controls. For each compound evaluated, rapamycin was also evaluated for the purpose of comparison. An IC50 was obtained for each test compound as well as for rapamycin. When evaluated as a comparator for the representative compounds of this invention, rapamycin had an $IC_{50}$ ranging from 0.4–5.1 nM. The results obtained are provided as an $IC_{50}$ and as the percent inhibition of T-cell proliferation at 0.1 µM. The results obtained for the representative compounds of this invention were also expressed as a ratio compared with rapamycin. A positive ratio indicates immunosuppressive activity. A ratio of greater than 1 indicates that the test compound inhibited thymocyte proliferation to a greater extent than rapamycin. Calculation of the ratio is shown below.

$$\frac{IC_{50} \text{ of Rapamycin}}{IC_{50} \text{ of Test Compound}}$$

Representative compounds of this invention were also evaluated in an in vivo test procedure designed to determine the survival time of pinch skin graft from male BALB/c donors transplanted to male $C_3H(H-2K)$ recipients. The method is adapted from Billingham R. E. and Medawar P. B., J. Exp. Biol. 28:385-402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days±S.D.) of the drug treatment group was compared with the control group. The following table shows the results that were obtained. Results are expressed as the mean survival time in days. Untreated (control) pinch skin grafts are usually rejected within 6–7 days. The results shown in Table 1 are based on a dose of 4 mg/kg of test compound. A survival time of 12.0±1.7 days was obtained for rapamycin at 4 mg/kg.

The following table summarizes the results of representative compounds of this invention in these two standard test procedures.

TABLE 1

EVALUATION OF IMMUNOSUPPRESSIVE ACTIVITY*

| Compound | LAF $IC_{50}$ (nM) | (ratio) | % Inhib.+ | Skin Graft (days ± SD) |
|---|---|---|---|---|
| Example 1 | 90.9 | 0.04 | 72 | 7.2 ± 0.4 |
| Example 2 | 10.0 | 0.44 | 95 | 10.2 ± 0.4 |
|  |  |  |  | 10.0 ± 0.6 |
| Example 3 | 99.0 | 0.05 | 51 |  |
| Example 4 | 41.9 | 0.01 | 82 |  |

*Calculation of the ratio was described supra.
+Percent inhibition of T-cell proliferation at 0.1 µM.

The results of these standard pharmacological test procedures demonstrate immunosuppressive activity both in vitro and in vivo for the compounds of this invention. The results obtained in the LAF test procedure indicates suppression of T-cell proliferation, thereby demonstrating the immunosuppressive activity of the compounds of this invention. The results obtained for representative compounds of this invention in preventing skin graft rejection further demonstrates their utility as immunosuppressive agents.

Based on the results of these standard pharmacological test procedures, the compounds are useful in the treatment or prevention of transplantation rejection such as kidney, heart, liver, lung, bone marrow, pancreas (islet cells), cornea, small bowel, and skin allografts, and heart valve xenografts; in the treatment of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

Based on the activity profile obtained, the compounds of this invention also are considered to have antitumor, antifungal activities, and antiproliferative activities. The compounds of this invention therefore also useful in treating solid tumors, fungal infections, and hyperproliferative vascular diseases such as restenosis and atherosclerosis.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The compounds of this invention can be formulated neat or with a pharmaceutical carder to a mammal in need thereof. The pharmaceutical carder may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carder is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a frugally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 $\mu g/kg$–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds of this invention.

EXAMPLE 1

Rapamycin 31,42-diester with (diethoxyphosphoryl)carbamic acid

To a solution of rapamycin (1.0 g; 1.1 mmol) in 5 ml anhydrous methylene chloride was added diethylphosphinyl isocyanate (0.72 g; 4.9 mmol) via syringe. The reaction mixture was allowed to stir under a nitrogen atmosphere at 0° C. for one hour and then concentrated under reduced pressure. The crude product was purified by flash chromatography (ethyl acetate, followed by 4% methanol in ethyl acetate, silica), affording the title compound as a white solid (0.76 g/55% yield).

IR (KBr) 3400, 2910, 1740, 1645, 1460, 1020 cm$^{-1}$. NMR (400 MHz; DMSO) $^1$H: δ9.4–9.18 (2-m, 2H, protons on nitrogen of carbamate at C-42 and C-31) 5.25 (m, 1H, H-28 resulting from carbamate at C-28) 4.37 (m, 1H, H-42 resulting from carbamate at C-42) 4.08–3.96 (m, 8H, methylene protons of diethoxyphosphoryl at C-42 and C-31 ) 1.25–1.15 (m, 12H, methyl protons of diethoxyphosphoryl at C-42 and C-31) MS (neg. ion FAB) m/z: 1271 (M−), 912, 894, 590, 331.

EXAMPLE 2

Rapamycin 42-ester with (diethoxyphosphoryl)carbamic acid

To a solution of rapamycin (5.0 g; 5.5 mmol) in 5 ml anhydrous methylene chloride was added diethylphosphinyl isocyanate (1.0 g; 5.5 mmol) via syringe. The reaction mixture was allowed to stir under a nitrogen atmosphere at 0° C. for three hours and was monitored by thin layer chromatography. After one hour the reaction mixture had changed from a light brown solution to a light brown viscous liquid. Additional methylene chloride was used to dissolve the crude product, which was then concentrated in vacuo to yield a yellow foam. Purification was accomplished by flash chromatography (ethyl acetate/hexanes, 10: 1; silica), to produce a white solid. Two subsequent flash chromatography columns (ethyl acetate; silica) were used to remove residual rapamycin. The title compound was isolated as a white solid (2.13 g; 36% yield; Rf=0.44 in ethyl acetate, silica GF).

IR (KBr) 3400, 2910, 1730, 1640, 1450, 1370, 1325, 1290, 1240, 1200, 1160, 1120-1100, 990, 890cm$^{-1}$. NMR (400 MHz; DMSO) $^1$H: δ9.24 (d, 1H, proton on nitrogen of carbamate at C-42) 4.42 (m, 1H, H-42 resulting from carbamate at C-42) 4.05 (m, 4H, methylene protons of diethoxyphosphoryl at C-42) 1.22 (m, 6H, methyl protons of diethoxyphosphoryl at C-42) C: δ153 (carbamate carbonyl carbon at C-42) 63 (methylene carbon of diethoxyphosphoryl at C-42) MS (neg. ion FAB) m/z: 1092 (M−), 912, 764, 590, 546, 475, 378, 321,297. Analysis for C$_{56}$H$_{89}$N$_2$O$_{17}$P.½H$_2$O. Calculated: C, 61.01; H, 8.23; N, 2.54. Found: C, 60.72; H 8.11; N, 2.43.

Rapamycin 42-ester with (diethoxyphosphoryl)carbamic acid (E)-27-O-(methyl)oxime To a solution of rapamycin 42-ester with (diethoxyphosphoryl) carbamic acid (860 mg; 0.79 mmol) in 6 ml methanol was added methoxylamine hydrochloride (66 mg; 0.79 mmol) and sodium aceta (65 mg; 0.79 mmol). The pale yellow reaction mixture was stirred at ambient temperature overnight and was monitored by thin layer chromatography. The following morning distilled water and ethyl acetate were added to the reaction mixture. The aqueous layer was extracted with ethyl acetate five times. The combined organic layers were dried over sodium sulfate, filtered, and concentrated in vacuo to yield a white solid. Purification was accomplished by high performance liquid chromatography (acetonitrile/water, 55% to 65% gradient; reversed phase phenyl column), producing the pure ∓E"isomer of the oxime as a white solid (120 mg; 20% yield; Rf=0.27 in acetonitrile/water, 70:30, RP-8).

IR (KBr) 3400, 2930, 1740, 1620, 1450, 1370, 1325, 1290-1240, 1200, 1165, 1100-1010, 990, 885 cm$^{-1}$. NMR (400 MHz; DMSO) $^1$H: δ9.23 (d, 1H, proton on nitrogen of carbamate at C-42) 5.27 (d, 1H, H-29 resulting from E-methoxime at C-27) 4.46 (m, 1H, H-42 resulting from carbamate at C-42) 4.00 (m, 4H, methylene protons of diethoxyphosphoryl at C-42) 3.68 (s, 3H, methoxime methyl protons at C-27) 3.14 (d, 1H, H-28 resulting from E-methoxime wrt C-27) 1.23 (t, 6H, methyl protons of diethoxyphosphoryl at C-42) C: δ158 (C-27) 153 (carbamate carbonyl carbon at C-42) 63 (methylene carbon of diethoxyphosphoryl at C-42) 61 (methoxime methyl carbon at C-27) MS (neg. ion FAB) m/z: 1121 (M−), 942, 590, 297. Analysis for C$_{57}$H$_{92}$N$_3$O$_{17}$P. Calculated: C, 61.00; H, 8.26; N, 3.74. Found: C, 61.69; H, 8.47; N, 3.33.

EXAMPLES 4

Rapamycin 42-ester with (diethoxyphosphoryl)carbamic acid (Z)-27-O-(methyl)oxime To a solution of rapamycin 42-ester with (diethoxyphosphoryl)carbamic acid (860 mg; 0.79 mmol) in 6 ml methanol was added methoxylamine hydrochloride (66 mg; 0.79 mmol) and sodium acetate (65 mg; 0.79 mmol). The pale yellow reaction mixture was stirred at ambient temperature overnight and was monitored by thin layer chromatography. The following morning distilled water and ethyl acetate were added to the reaction mixture. The aqueous layer was extracted with ethyl acetate five times. The combined organic layers were dried over sodium sulfate, filtered, and concentrated in vacuo to yield a white solid. Purification was accomplished by high performance liquid chromatography (methanol/water, 85:15; reversed phase C-18 column), producing the pure "Z" isomer of the oxime as a white solid (180 mg; 20% yield; Rf =0.41 in acetonitrile/water, 70:30, RP-8).

IR (KBr) 3400, 2930, 1740, 1645, 1450, 1370, 1330, 1290-1230, 1200, 1165, 1100–1020, 990, 890 cm$^{-1}$. NMR (400MHz;DMSO) $^1$H: δ9.26 (d, 1H, proton on nitrogen of carbamate at C-42) 4.50 (m, 1H, H-42 resulting from carbamate at C-42) 4.04 (m, 4H, methylene protons of diethoxyphosphoryl at C-42) 3.90 (m, 1H, H-28 resulting from Z-methoxime at C-27) 3.75 (s, 3H, methoxime methyl protons at C-27) 1.24 (t, 6H, methyl protons of diethoxyphosphoryl at C-42) C: δ158 (C-27) 153 (carbamate carbonyl carbon at C-42) 63 (methylene carbon of diethoxyphosphoryl at C-42) 61 (methoxime methyl carbon at C-27) MS (neg. ion FAB) m/z: 1121 (M−), 942, 590, 297. Analysis for C$_{57}$H$_{92}$N$_3$O$_{17}$P. Calculated: C, 61.00; H, 8.26; N, 3.74. Found: C, 60.76; H, 8.36; N, 3.39.

What is claimed is:

1. A compound of the structure

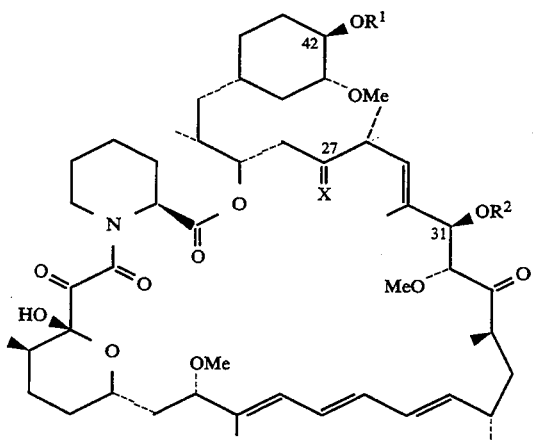

wherein R$^1$ and R$^2$ are each, independently, hydrogen, or

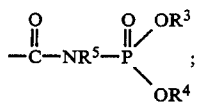

R$^3$ and R$^4$ are each, independently, hydrogen, Ar, or —(CR$^6$R$^7$)$_a$Y(CR$^8$R$^9$)$_b$Z, or R$^3$ and R$^4$ may be taken together to form a 5–7 membered ring; wherein when R$^3$ and R$^4$ are taken together to form a 5–7 membered ring, R$^3$R$^4$ are —(CH$_2$)$_2$—, or —(CH$_2$)$_3$—, or —(CH$_2$)$_4$—;

R$^5$ is hydrogen, alkyl of 1–6 carbon atoms, alkenyl of 2–7 carbon atoms, alkynyl of 2–7 carbon atoms, alkoxyalkyl of 2–7 carbon atoms, arylalkyl of 7–10 carbon atoms, cycloalkyl of 3–8 carbon atoms, or Ar;

R$^6$, R$^7$, R$^8$, and R$^9$, are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, —OR$^{10}$, —SR$^{10}$, halogen, —CN, —NO$_2$, —CF$_3$, —COR$^{10}$, —CO$_2$R$^{10}$, —CONHR$^{10}$, —SO$_2$R$^{10}$, —SO$_3$R$^{10}$, —OSO$_3$R$^{10}$, —NR$^{10}$R$^{11}$, —NHCOR$^{10}$, —NHCO$_2$R$^{10}$, —NHSO$_2$R$^{10}$, —NHSO$_3$R$^{10}$, or Ar;

X is O or NOR$^{12}$;

Y is —O—, —CH$_2$—, —NR$^{13}$—, —S—, —S(O)—, —S(O)$_2$—, or —C(O)—;

R$^{10}$, R$^{11}$, R$^{12}$, and R$^{13}$ are each, independently, hydrogen, alkyl of 1–6 carbon atoms, or arylalkyl of 7–10 carbon atoms;

Z is hydrogen, alkyl of 1–6 carbon atoms, or Ar;

Ar is a phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, benzopyranyl, benz[b]thiophenolyl, benzimidazolyl, benzthiazolyl, benzodioxolyl, piperidyl, morpholinyl, piperazinyl, tetrahydrofuranyl, or pyrrolidinyl group which may be optionally mono-, di-, or tri-substituted with a group selected from alkyl of 1–6 carbon atoms, alkoxy of 1–6 carbon atoms, cyano, halo, hydroxy, nitro, carbalkoxy of 2-carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H;

wherein the aryl moiety of the arylalkyl group of R$^5$, R$^6$, R$^7$, R$^8$, R$^9$R$^{10}$, R$^{11}$, R$^{12}$, and R$^{13}$ is selected from the group consisting of phenyl naphthyl, pyridyl quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, benzopyranyl, benz[b]thiophenolyl, benzimidazolyl, benzthiazolyl, benzodioxolyl, piperidyl, morpholinyl, piperazinyl, tetrahydrofuranyl, and pyrrolidinyl;

a = 1–6 and;

b = 0–6;

or a pharmaceutically acceptable salt thereof, with the proviso that R$^1$ and R$^2$ are not both hydrogen; and further provided that when a is greater than 1, each of the (CR$^6$R$^7$) subunits may be the same or different and when b is greater than 1, each of the (CR$^8$R$^9$) may be the same or different.

2. The compound according to claim 1 wherein R$^3$ and R$^4$ are alkyl of 1–6 carbon atoms or a pharmaceutically acceptable salt thereof.

3. The compound according to claim 1 where in R$^5$ is hydrogen or a pharmaceutically acceptable salt thereof:

4. The compound according to claim 1 wherein R$^2$ and R$^5$ are hydrogen or a pharmaceutically acceptable salt thereof.

5. The compound according to claim 1 wherein R$^2$ and R$^5$ are hydrogen and R$^3$ and R$^4$ are alkyl of 1–6 carbon atoms or a pharmaceutically acceptable salt thereof.

6. The compound according to claim 1 which is rapamycin 31,42-diester with (diethoxyphosphoryl)carbamic acid or a pharmaceutically acceptable salt thereof.

7. The compound according to claim 1 which is rapamycin 42-ester with (diethoxyphosphoryl)carbamic acid or a pharmaceutically acceptable salt thereof.

8. The compound according to claim 1 which is rapamycin 42-ester with (diethoxyphosphoryl)carbamic acid (E)-27-O-(methyl)oxime or a pharmaceutically acceptable salt thereof.

9. The compound according to claim 1 which is rapamycin 42-ester with (diethoxyphosphoryl)carbamic acid (Z)-27-O-(methyl)oxime or a pharmaceutically acceptable salt thereof.

* * * * *